(12) United States Patent
Waldron et al.

(10) Patent No.: US 7,893,047 B2
(45) Date of Patent: Feb. 22, 2011

(54) BIOCIDE COMPOSITION COMPRISING PYRITHIONE AND PYRROLE DERIVATIVES

(75) Inventors: Craig Waldron, Marietta, GA (US); Robert Martin, Monroe, CT (US); Gareth Williams, Kirkbymoorside York (GB); Tina Williams, legal representative, Kirkbymoorside York (GB)

(73) Assignee: Arch Chemicals, Inc., Norwalk, CT (US)

(*) Notice: Subject to any disclaimer, the term of this patent is extended or adjusted under 35 U.S.C. 154(b) by 598 days.

(21) Appl. No.: 11/368,244

(22) Filed: Mar. 3, 2006

(65) Prior Publication Data

US 2007/0207178 A1    Sep. 6, 2007

(51) Int. Cl.
*A01N 55/02* (2006.01)
*A61K 31/555* (2006.01)

(52) U.S. Cl. .................................................... 514/186
(58) Field of Classification Search .................. 514/408
See application file for complete search history.

(56) References Cited

U.S. PATENT DOCUMENTS

| | | | | |
|---|---|---|---|---|
| 2,786,847 A | 3/1957 | Cislak | ...................... | 260/294.8 |
| 2,809,971 A | 10/1957 | Berstein et al. | ............. | 260/270 |
| 3,589,999 A | 6/1971 | McRae et al. | .................. | 210/28 |
| 3,615,744 A | 10/1971 | Yokoo et al. | .................... | 106/15 |
| 3,773,770 A | 11/1973 | Damico | ....................... | 260/290 |
| 4,039,312 A | 8/1977 | Patru | .............................. | 71/67 |
| 4,399,130 A | 8/1983 | Davidson et al. | ............. | 424/245 |
| 4,496,559 A | 1/1985 | Henderson et al. | .......... | 514/188 |
| 4,565,856 A | 1/1986 | Trotz et al. | ................... | 526/265 |
| 4,581,351 A | 4/1986 | Berke et al. | ................. | 514/188 |
| 4,610,993 A | 9/1986 | Wedig et al. | ................. | 514/335 |
| 4,957,658 A | 9/1990 | French et al. | .......... | 252/400.23 |
| 5,057,153 A * | 10/1991 | Ruggiero | .................. | 106/18.33 |
| 5,098,473 A | 3/1992 | Hani et al. | ................ | 106/18.33 |
| 5,112,397 A | 5/1992 | Farmer, Jr. et al. | ....... | 106/18.33 |
| 5,137,569 A | 8/1992 | Waldron et al. | .......... | 106/18.33 |
| 5,185,033 A | 2/1993 | Hani et al. | ................ | 106/18.33 |
| 5,232,493 A | 8/1993 | Waldron et al. | .......... | 106/18.33 |
| 5,238,490 A | 8/1993 | Farmer, Jr. et al. | ....... | 106/18.33 |
| 5,246,489 A | 9/1993 | Farmer, Jr. et al. | ....... | 106/18.33 |
| 5,252,123 A | 10/1993 | Hani et al. | ................ | 106/18.33 |
| 5,298,061 A | 3/1994 | Waldron et al. | .......... | 106/18.33 |
| 5,310,938 A * | 5/1994 | Brown et al. | ................. | 548/557 |
| 5,328,928 A * | 7/1994 | Addor et al. | ................. | 514/423 |
| 5,342,437 A | 8/1994 | Gavin et al. | .............. | 106/18.33 |
| 5,712,275 A | 1/1998 | Van Gestel | ............... | 514/222.5 |
| 5,717,007 A | 2/1998 | Cambon | ...................... | 523/122 |
| 5,932,520 A | 8/1999 | Van der Flass et al. | ...... | 504/156 |
| 6,069,189 A | 5/2000 | Kramer et al. | .............. | 523/122 |
| 6,228,382 B1 | 5/2001 | Lindner et al. | .............. | 424/405 |
| 6,710,117 B2 | 3/2004 | Gillard et al. | ............... | 524/530 |
| 2003/0162924 A1 | 8/2003 | Vos et al. | ..................... | 526/264 |

FOREIGN PATENT DOCUMENTS

| | | |
|---|---|---|
| EP | 610251 | 8/1997 |
| EP | 0658181 B1 | 1/1998 |
| EP | 0658180 B1 | 10/1998 |
| EP | 0700422 B1 | 11/1998 |
| EP | 0927230 B1 | 6/2001 |
| EP | 0775733 B1 | 4/2002 |
| EP | 746979 | 7/2004 |
| WO | 95/10568 | 4/1995 |
| WO | 98/12269 | 3/1998 |
| WO | 03/039256 | 5/2003 |
| WO | WO-03/039256 * | 5/2003 |

* cited by examiner

*Primary Examiner*—Alton N Pryor
(74) *Attorney, Agent, or Firm*—Dale L. Carlson; Wanli Wu; Wiggin and Dana LLP

(57) ABSTRACT

The present invention is directed to a biocidal composition comprising a blend of one or more pyrithione compounds, and one or more pyrrole compounds of Formula I wherein said biocidal composition is copper free or low copper content.

8 Claims, No Drawings

BIOCIDE COMPOSITION COMPRISING PYRITHIONE AND PYRROLE DERIVATIVES

BACKGROUND OF THE INVENTION

1. Field of the Invention

This invention relates to a biocidal composition. More particularly, this invention relates to a biocidal composition comprising a blend of at least one selected pyrithione compounds and at least one selected pyrrole derivatives that prevent, or inhibit growth of microbes and the method of using such biocidal composition.

2. Brief Description of Art

Many compositions and formulations are known in the art for the prevention, inhibition, and treatment of growth or infestation of microbes. Likewise, there are many compositions and coatings specifically formulated for the prevention, inhibition, and treatment of growth or infestation of fouling organisms.

Fouling organisms present a large problem for substrates and objects that are exposed to water. The term "fouling organism" includes both hard and soft fouling organisms. Hard fouling organisms include barnacles, mollusks, and the like, while soft fouling organisms include algae, fungi, and the organisms listed in U.S. Pat. No. 5,712,275, which is incorporated by reference herein. Such organisms present a constant problem for objects and substrates that are exposed to marine water, fresh water, brackish water, sewage water, waste water, rain water, and the like.

Fouling organisms grow on, infest, or adhere to various kinds of substrates and objects that are exposed to any type of water. Growth or infestation of fouling organisms on surfaces is visually unappealing. Additionally, growth may cause some problems in using the substrates and objects that fouling organisms have attached or infested. For example, one problem that occurs frequently is the attachment of hard fouling organisms to a ship hull. The organisms cause the surface of the ship to become rough, thereby reducing the ship's speed.

Additionally, wood and wood products often experience growth and infestation of microbes such as fouling organisms, termites and the like. Growth and infestation of such microbes leads to warping, cracking, and deterioration of the wood and wood products. Consequently the wood and wood products lose value, visual appeal, and usefulness.

To combat this problem, coatings comprising biocides were developed. Examples of biocides found useful include tributylin compounds, pyrithione compounds, oxathiazine compounds, pyrrole compounds, triphenylboron compounds and terbutyn.

Pyrithione compounds and select pyrrole compounds are separately known and used as biocidal or antifouling agents. However, it is not known in the art, nor is it obvious to combine the two compounds. Examples of prior art references teaching the use of pyrithione compounds and selected pyrrole compounds include the following:

U.S. Pat. No. 5,057,153 to Ruggiero relates to an improved paint or paint base composition characterized by enhanced biocidal efficacy. The paint contains a biocide comprising pyrithione salt and a copper salt. Additionally, in U.S. Pat. No. 5,246,489 to Farmer Jr. et al. a process for generating copper pyrithione biocide in-situ in a paint formulation is disclosed. The paint and paint bases of this patent comprise pyrithione compounds as the only biocide present in the formulation.

U.S. Pat. No. 5,098,473 to Hani et al. relates to paints and paint bases, and more specifically to a process for providing a stable gel-free dispersion of zinc pyrithione plus cuprous oxide biocide in paint (see also U.S. Pat. Nos. 5,098,473; 5,112,397; 5,137,569; 5,185,033; 5,232,493; 5,298,061; 5,342,437; PCT Patent Application No. WO 95/10568 and EP 0610251).

U.S. Pat. No. 4,957,658 to French et al. related to paint and paint bases and more specifically to a process and composition for providing reduced discoloration of paints and paint bases containing a pyrithione and ferric ion.

U.S. Pat. No. 4,399,130 to Davidson et al. describes a method using an effective amount of at least one metallic salt of pyridine-2-thione-N-oxide to treat or prevent swine exudate epidermitis.

U.S. Pat. No. 4,496,559 to Henderson et al. describes selected derivatives of 2-selenopyridine-N-oxide for use as fungicides and bactericides.

U.S. Pat. No. 4,565,856 to Trotz et al. relates to pyrithione-containing polymers. The polymers described in this patent are used as biocides in paints and wood preservative products.

U.S. Pat. No. 4,610,993 to Wedy et al. describes a method of administering an effective mount of at least one selected pyridine-N-oxide disulfide compound to treat or prevent bovine mastitis.

European patent number EP 0746979 describes a method for controlling or combating the attachment of a fouling organism to an underwater surface by contacting the organism with an antifouling-effective amount of a 2-arylpyrrole compound.

U.S. Pat. No. 6,069,189 to Kramer et al., describes antifouling paints that contain selected pyrrole derivatives. Specific pyrrole compounds incorporated into the antifouling paint include 2-trihalogenomethyl-3-halogeno-4-cyano pyrrole and derivatives thereof. Kramer et al. found these compounds to be particularly effective against barnacle infestation. Additionally, this Kramer et al. reference found that bright or light colored anti-fouling paint could be created despite the addition of these compounds.

PCT Patent Application No. WO 03/039256 describes an antifouling composition that comprises an amount of at least 3.5 wt. % based on the total weight of the dry mass of the composition of 4-bromo-2-(4-chlorophenyl)-5-(trifluoromethyl)-1H-pyrrole-3-carbonitrile, or a salt thereof together with another biocide. The other biocide is selected from bethoxazin, tolyfluanide, dichlofuanide, or DCOIT.

Despite the advances made in the art, what is still needed is a coating that comprises an biocidal composition that would be effective against a large spectrum of microbes, and also demonstrates high durability and low toxicity. Ideally, the coating and the composition would be easily and inexpensively produced. This invention is believed to be an answer to the above discussed problems.

BRIEF SUMMARY OF THE INVENTION

Therefore, one aspect of the present invention is directed to a biocidal composition comprising one or more pyrithione compounds, and one or more pyrrole compounds of Formula I:

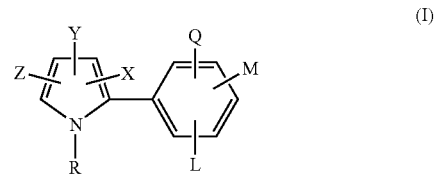

wherein X is halogen, CN, $NO_2$ or $S(O)_nR_1$; Y is hydrogen, halogen or $S(O)_nR_1$; Z is halogen, $C_1$-$C_4$haloalkyl or $S(O)_nR_1$; n is an integer of 0, 1 or 2; $R_1$ is $C_1$-$C_4$haloalkyl; L is hydrogen or halogen; M and Q are each independently hydrogen, halogen, $C_1$-$C_4$alkyl, $C_1$-$C_4$haloalkyl, $C_1$-$C_4$alkoxy, $C_1$-$C_4$alkylthio, $C_1$-$C_4$alkylsulfinyl, $C_1$-$C_4$alkylsulfonyl, CN, NO$_2$, R$_2$CO or NR$_3$R$_4$, or when M and Q are on adjacent positions and are taken together with the carbon atoms to which they are attached MQ represents the structure —OCH$_2$O—, —OCF$_2$O—, or —CH═CH—CH═CH—; R is hydrogen, C$_1$-C$_4$alkoxyalkyl, C$_1$-C$_4$alkythioalkyl or R$_6$CO; R$_2$ is C$_1$-C$_4$alkyl, C$_1$-C$_4$haloalkyl, C$_1$-C$_4$alkoxy or NR$_3$R$_4$; R$_3$ is hydrogen or C$_1$-C$_4$alkyl; R$_4$ is hydrogen, C$_1$-C$_4$alkyl or R$_5$CO; R$_5$ is hydrogen or C$_1$-C$_4$alkyl; and R$_6$ is C$_1$-C$_4$alkyl, C$_1$-C$_4$haloalkyl, C$_1$-C$_4$alkoxy, C$_2$-C$_6$ alkenyloxy, C$_1$-C$_4$haloalkoxy, phenyl optionally substituted with one to three C$_1$-C$_4$alkyl groups, benzyl, phenoxy, benzyloxy, C$_1$-C$_4$alkylcarbonyloxy, C$_3$-C$_6$cycloalkyl, naphthyl, pyridyl, thienyl or furanyl, wherein said biocidal composition is copper free or low copper content.

As defined herein, the term halogen designates Cl, Br, I or F, and the term haloalkyl designates any alkyl group C$_n$H$_{2n+1}$ having from 1 halogen atom to 2n+1 halogen atoms wherein the halogen atoms are the same or different.

Another aspect of the present invention is directed to a coating composition comprising an effective biocidal amount of a biocidal composition comprising one or more pyrithione compounds and one or more pyrrole compounds of Formula (I) as described above wherein said biocidal composition is copper free or low copper content.

Still another aspect of the present invention is directed to a method of coating a substrate comprising applying a coating composition that contains a biocidal composition comprised of one or more pyrithione compounds and one or more pyrrole compounds of Formula (I) as described above, to the substrate and drying the coating composition on the substrate.

Yet another aspect of the present invention is directed to a coated substrate comprising the coating composition that contains a biocidal composition of the present invention and a substrate, wherein said substrate is selected from a group consisting of wood, plastic, leather, vinyl and metal.

One expected advantage of the present invention includes increased protection against a large spectrum of microbes. Another expected advantage of the present invention includes preservation of wood and wood-products. Additionally, it is expected that the present invention will be long-lasting, have low toxicity, and be easily and inexpensively produced.

DETAILED DESCRIPTION OF THE INVENTION

The term "an effective biocidal amount" as used in the present specification and claims relates to the amount of the biocidal composition that has a positive effect on reducing, eliminating, or preventing attachment or growth of microbes on a substrate.

The term "microbe" as used in the present specification and claims includes algae, fungi, biofilm, insects, fouling organisms (including both hard and soft fouling organisms), or any organism that can attach to, grow on, or damage materials such as wood, concrete, paper, plastic, and the like.

The term "copper free or low copper content" as used in the present specification and claims means that the compositions do not contain copper or contain copper at a total weight percent of less than 3% by weight, based on the total weight of formulation.

The term "wood products" as used in the present specification and claims includes materials that contain or are derived from wood, including, but not limited to, particle board, chipboard, plywood, wafer board, wood laminated material, pressed wood, and the like.

As indicated above, one aspect of the present invention is a biocidal composition comprising one or more pyrithione compounds and one or more pyrrole compounds according to Formula (I) as described above. Each of these components is discussed in more detail below.

Pyrithiones in general are widely known and frequently used in a variety of applications including paint and personal care products. Pyrithiones are excellent biocides, and can be found in antifouling marine paint. Additionally, metal salts of pyrithione including tin, cadmium and zirconium, are suitable for use in shampoo.

Preferably, the pyrithione in the biocidal composition are compounds with the following basic structure:

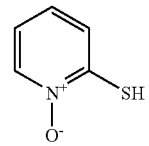

Pyrithione compounds suitable for use in the present invention include zinc pyrithione, copper pyrithione, sodium Omadine®, pyridine-N-oxide disulfide, Omadine® disulfide, 2,2'-dithio-pyridine-1,1-dioxide, or pyridine-2-thione-N-oxide. Such pyrithione compounds have excellent biocidal effects. Zinc and copper pyrithione are most preferable because of the low soluable in salt water therefore making it more durable than other pyrithione salts.

The zinc and copper pyrithione compounds can be prepared by methods described in U.S. Pat. No. 2,809,971 to Berstein et al. Other patents disclosing similar compounds and processes for making them include U.S. Pat. Nos. 2,786,847; 3,589,999; and 3,773,770.

Additionally, the biocidal composition of the present invention comprises one or more pyrrole compounds of Formula (I) as shown above. Preferably, the pyrrole compounds are 2-trihalogenomethyl-3-halogeno-4-cyano pyrrole derivatives substituted in position 5 and optionally in position 1, the halogens in positions 2 and 3 being independently selected from the group consisting of fluorine, chlorine and bromine, the substituent in position 5 being selected from the group consisting of phenyl, mono- and dihalogenophenyl, mono- and di-C1-4 alkyl phenyl, and monohalogeno mono-C1-4 alkyl phenyl, any halogen on the substituent in position 5 being selected from the group consisting of chlorine and bromine, the optional substituent in position 1 being selected from C1-4 alkyl and C1-4 alkoxy C1-4 alkyl. Among the 2-arylpyrrole compounds suitable for use in the methods and composition of the invention are: 4,5-dichloro-2-(alpha,alpha,alpha-trifluoro-p-tolyl)pyrrole-3-carbonitrile; 4-bromo-5-chloro-2-(p-chlorophenyl)pyrrole-3-carbonitrile; 4-bromo-2-(p-chlorophenyl)-5-(trifluoromethyl)pyrrole-3-carbonitrile; 3,4-dichloro-2-(3,4-dichlorophenyl)pyrrole-5-carbonitrile; 4-chloro-2-(p-chlorophenyl)-5-(trifluoromethyl)pyrrole-3-carbonitrile; 4,5-dibromo-2-(p-chlorophenyl)-3-(trifluoromethylsulfonyl)pyrrole; 4-bromo-2-(3,5-dichlorophenyl)-5-(trifluoromethyl)pyrrole-3-carbonitrile; 2-(p-chlorophenyl)-5-(trifluoromethyl)-4-(trifluoromethylthio)pyrrole-3-carbonitrile; 4-bromo-2-(2,3,4-trichlorophenyl)-5-(trifluoromethyl)pyrrole-3-carbonitrile; 4-bromo-2-(2,3,5-trichlorophenyl)-5-(trifluoromethyl)-pyrrole-3-carbonitrile; 4-bromo-2-(p-chlorophenyl)-5-(alpha,alpha,beta,beta-tetrafluoroethylthio) pyrrole-3-carbonitrile; 4-bromo-2-(m-fluorophenyl)-5-(trifluoromethyl)pyrrole-3-carbonitrile; 2-(3,5-dichlorophenyl)-5-(trifluoromethyl)-4-(trifluoromethylthio) pyrrole-3-carbonitrile; and 4-bromo-2-(p-chlorophenyl)-5-[(beta-bromo-beta,alpha,alpha-trifluoro)-ethylthio]pyrrole- 3-carbonitrile. Most preferably, Formula (I) is 4-bromo-2-(4-chlorophenyl)-5-(trifluoromethyl)-1H-pyrrole-3-carbonitrile.

The compounds of Formula (I) as discussed above can be prepared by methods described in U.S. Pat. Nos. 5,310,938 and 5,328,928.

To ensure biocidal effectiveness, the pyrithione compounds and the compounds of Formula (I) are preferably present in the biocidal composition in a weight ratio of 9:1 to 1:9. More preferably, the pyrithione compounds and compounds of Formula (I) are present in the biocidal composition in a weight ratio of 3:2 to 2:3. Most preferably, the pyrithione compounds and the compounds of Formula (I) are present in the biocidal composition in a weight ratio of 3:1 to 1:3.

Another aspect of the invention comprises a coating composition that contains the above biocidal composition. The biocidal composition is present in the coating composition in an effective biocidal amount. The effective biocidal amount is between 1%-15% by weight, based on the total weight of the coating composition. Preferably, the biocidal composition is present in an amount between 1% and 15% by weight, based on the total weight of the coating composition. More preferably, the biocidal composition is present in an amount between 1% and 10% by weight, based on the total weight of the coating composition. Most preferably, the biocidal composition is present in an amount between 3% and 8% by weight, based on the total weight of the coating composition.

In addition to the biocidal composition, the coating composition may also include additives. Such additives may include, but are not limited to, organic binding agents; processing additives; fixatives such as polyvinyl alcohol; plasticizers; UV stabilizers; dyes; color pigments; anti-settling agents; antifoaming agents; additional insecticides such as chlorinated hydrocarbons, organophosphates and the like; additional fungicides and bactericides such as alcohols, aldehydes, formaldehyde releasing compounds, and the like; phenols; organic acids such as propionic acid, benzoic acids and the like; inorganic acids such as boric acid; amides; azoles; heterocyclic compounds; N-haloalkylthio compounds; and the like. Polymers, such as acrylic polymers or acrylic co-polymers, that are self-polishing for use in, for example, marine antifouling coatings may also be employed. Preferably, these polymers are free of tin. Examples of acrylic polymers and copolymers that may be implemented in the composition of the invention include copper acrylate polymer or co-polymer, zinc acrylate polymer or co-polymer, silyl acrylate polymer or co-polymer, and the like. Additional polymers known in the paint and coating arts may also be employed in the composition of the invention. The additives present in the coating composition will depend on the preferences of the user or manufacturer as well as the end use of the coating composition.

The coating composition is formed by combining the biocidal composition and additives into a paint base material, such as a marine paint base. Methods of forming such a coating composition are well known in the art. Examples of such methods include, but are not limited to combining the biocidal composition and the additives in a blending mechanism. The blending mechanism would evenly disperse the biocidal composition throughout the additives. Additional methods of forming the coating composition can be used as known to those skilled in the art. In addition, any base paint material that is suitable for marine applications, including water or solvent-based formulations, may be used in the coating composition of the invention. Such marine paints are known in the art, as shown, for example, in U.S. Pat. Nos. 6,710,117; 4,981,946; 4,426,464; 4,407,997; and 4,021,392.

The coating composition can take a variety of forms. Those forms include, but are not limited to paint, (especially antifouling paint), varnish, lacquer, a wash, a wood sealant, or any form that may be used to coat the material.

Another aspect of the invention comprises a method comprising applying the coating composition described above to material being sought to protect. The coating composition may be applied in a variety of manners that include, but are not limited to, brushing on, spraying on, sponging on, atomizing on, or dipping, immersing, or soaking the material in. Preferably the coating composition is applied in an even fashion to the material. Once the coating composition is applied to the material, it should be allowed to dry to ensure proper adhesion to the material. Drying can be accomplished by exposure to the air, or by using a mechanism that allows for faster drying such as heat lamps, or a hot air generator.

Material that can be protected by the coating composition includes wood, leather, vinyl, plastic, concrete, plaster, paper, and any other material that may be exposed to microbes or to water containing such microbes. Ideally, the material should be porous enough to allow the coating composition to penetrate and adhere to the material.

Another aspect of the invention comprises a coated substrate. The coated substrate comprises a material as described above that has been coated with the coating composition. Substrates that would benefit the most from application of the coating composition include traditional marine substrates such as ship hulls, docks, piers, buoys, fishing gear, fishnets, lobster traps, bridges, and pilings. However, substrates coated with the coating composition may also include concrete, wallboard, decks, siding, or any other substrate that is in constant or frequent contact with water or microbes.

The substrate is expected to exhibit biocidal properties when it is coated with the coating composition. The biocidal properties will prevent, inhibit, or treat attachment or growth of microbes on or in the substrate. Prevention or treatment of such growth will allow the substrate to be microbe free. In addition to the substrate being visually appealing, being microbe free will allow it to be used in the manner it was intended to be used.

Additionally, it is expected that wood or wood products that are coated with the coating composition will exhibit resistance to microbes. Application of the coating composition to wood and wood products is expected to prevent microbes such as fungi, algae, termites, and the like from destroying the visual appeal and use of the wood and wood products. Commercial and residential products and structures that would benefit from such application include staircases, floors, cabinets, decks, piers, shingles, pilings, fences, furniture, mailboxes, and the like.

EXAMPLES

The following Examples further illustrate the present invention. All parts and percentages are by weight unless explicitly stated otherwise. All temperatures are degrees Celsius unless explicitly stated otherwise.

Paint Efficacy Testing

A series of nine paint formulations containing 4-bromo-2-(4-chlorophenyl)-5-(trifluoromethyl)-1H-pyrrole-3-carbonitrile (referred to in below table as Pyrrole) and zinc pyrithione (ZPT) were tested by Duke University off the Beaufort, N.C. coast in 2004 for their antifouling effectiveness against barnacles and other fouling organisms. The formulations were created in the laboratory by the addition of various amounts of biocides to a resin base-formulation (vinyl resin/wood rosin with Zn oxide filler). Formulations include 4-bromo-2-(4-chlorophenyl)-5-(trifluoromethyl)-1H-pyrrole-3-carbonitrile alone and in combination with ZPT. A solvent based zinc oxide coating was used as a control. Unprimed fiberglass rods (8 mm diameter×11 cm length) were dip-coated with each formulation (5 rods/formulation) and suspended from a test rack in the ocean (one-meter below the surface). Rods were evaluated each month for number of barnacles and bryozoans. The most promising results came from the formulations in which 4-bromo-2-(4-chlorophenyl)-5-(trifluoromethyl)-1H-pyrrole-3-carbonitrile was blended with ZPT (See Table 1 below).

Bryozoans are highly complex colonial animals constructed of individual "zooids", all connected by living tissue. The zooids are protected within a cup- or box-shaped exoskeleton of calcified chitinous tissue. The degree of calcification governs how rigid or flexible is the overall structure. Bryozoans are eaten by a variety of grazing animals, such as sea urchins and various molluscs.

The study confirms that 4-bromo-2-(4-chlorophenyl)-5-(trifluoromethyl)-1H-pyrrole-3-carbonitrile is an effective antifouling agent for hard fouling organisms such as barnacles, that it is compatible with ZPT, and that it performs better with ZPT as a co-biocide than it does alone.

zinc acrylate polymer or co-polymer, silyl acrylate polymer or co-polymer, and combinations thereof.

3. A coating composition comprising an effective biocidal amount of a synergistic biocidal composition comprising:
A) zinc pyrithione; and
B) 4-bromo-2-(4-chlorophenyl)-5-(trifluoromethyl)-1H-pyrrole-3-carbonitrile
wherein zinc pyrithione and 4-bromo-2-(4-chlorophenyl)-5-(trifluoromethyl)-1H-pyrrole-3-carbonitrile are present in a weight ratio of 3:2 to 2:3;
wherein the effective biocidal amount is between 1% and 15% by weight, based on the total weight of said coating composition, and
wherein said biocidal composition is copper free or low copper content.

4. The coating composition of claim 3, wherein the effective biocidal amount is between 2% and 10% by weight, based on the total weight of said coating composition.

TABLE 1

| DATES | | 2 months Average Jul. 16, 2004 | | 3 months Average Aug. 13, 2004 | 4 months Average Sep. 15, 2004 | | 5 months Average Oct. 13, 2004 | |
|---|---|---|---|---|---|---|---|---|
| CODE | ROD # | Bryozoans | # of BARNACLES | # of BARNACLES | Bryozoans | # of BARNACLES | Bryozoans | # of BARNACLES |
| CONTROL - No Biocide | 1 | 7.8 | 18.2 | 0 | 14 | 4 | 14.5 | M | M |
| 8% Pyrrole Biocide | 2 | 0.4 | 1 | 0 | 4 | 2.2 | 8.6 | M | 1 |
| 6% Pyrrole Biocide | 3 | 0.4 | 1.4 | 0 | 7 | 0.6 | 5.6 | 0.2 | 0.8 |
| 4% Pyrrole Biocide | 4 | 0 | 0.8 | 0 | 5.6 | 0.4 | 4 | 0.4 | 1.6 |
| 5% Pyrrole 4% ZPT | 5 | 0 | 0.4 | 0 | 1 | 0 | 3.4 | 0 | 0.8 |
| 5% Pyrrole 2% ZPT | 6 | 0 | 0.6 | 0 | 1.8 | 0 | 1.4 | 0 | 0.4 |
| 2% Pyrrole | 7 | 0 | 1 | 0 | 16 | 0 | 3.2 | 0.2 | 1.2 |
| 2% Pyrrole 4% ZPT | 8 | 0 | 0.2 | 0 | 12.2 | 0.4 | 4.4 | 0 | 2 |
| 2% Pyrrole 2% ZPT | 9 | 0 | 0.8 | 0 | 9.4 | 0 | 3.8 | 0 | 1.2 |

Notes:
"M" refers to a mature fouling community. The growth cycle of certain marine organisms can cause a difference in the average number per month reading in the above table.

While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entireties.

What is claimed is:

1. A biocidal composition comprising:
A.) zinc pyrithione, and
B.) 4-bromo-2-(4-chlorophenyl)-5-(trifluoromethyl)-1H-pyrrole-3-carbonitrile;
wherein zinc pyrithione and 4-bromo-2-(4-chlorophenyl)-5-(trifluoromethyl)-1H-pyrrole-3-carbonitrile are present in a weight ratio of 3:2 to 2:3; and
wherein said biocidal composition is copper free or low copper content.

2. The biocidal composition of claim 1, further comprising at least one acrylic polymer or co-polymer selected from the group consisting of copper acrylate polymer or co-polymer, 5. The coating composition of claim 4, wherein the effective biocidal amount is between 3% and 8% by weight, based on the total weight of said coating composition.

6. The coating composition of claim 3, further comprising at least one acrylic polymer or co-polymer selected from the group consisting of copper acrylate polymer or co-polymer, zinc acrylate polymer or co-polymer, silyl acrylate polymer or co-polymer, and combinations thereof.

7. A coating composition, comprising:
a synergistic biocidal composition, comprising from about 2 to about 4 wt % of zinc pyrithione compound, based on the total weight of said coating composition and from about 2 to about 5 wt % of 4-bromo-2-(4-chlorophenyl)-5-(trifluoromethyl)-1H-pyrrole-3-carbonitrile, based on the total weight of said coating composition; said biocidal composition being substantially copper-free or containing copper at a total weight percent of less than 3% by weight, based on the total weight of the composition; and
a marine paint base;

wherein said zinc pyrithione and said 4-bromo-2-(4-chlorophenyl)-5-(trifluoromethyl)-1H-pyrrole-3-carbonitrile are present in said coating composition in a weight ratio of from 3:2 to 2:3.

8. A synergistic biocidal composition comprising:
(A) zinc pyrithione, and
(B) a pyrrole compound being 4-bromo-2-(4-chlorophenyl)-5-(trifluoromethyl)-1H-pyrrole-3-carbonitrile;

wherein the zinc pyrithione and the pyrrole compound are present in a weight ratio of 3:2 to 2:3; and wherein the biocidal composition is substantially copper-free or contain copper at a total weight percent of less than 3% by weight, based on the total weight of the composition.

* * * * *

UNITED STATES PATENT AND TRADEMARK OFFICE
CERTIFICATE OF CORRECTION

| | |
|---|---|
| PATENT NO. | : 7,893,047 B2 |
| APPLICATION NO. | : 11/368244 |
| DATED | : February 22, 2011 |
| INVENTOR(S) | : Craig Waldron, Robert Martin and Gareth Williams |

It is certified that error appears in the above-identified patent and that said Letters Patent is hereby corrected as shown below:

In claim 3, column 8, line 4, "synergistic" should be deleted.

In claim 7, column 8, line 56, "synergistic" should be deleted.

In claim 9, column 9, line 5, "synergistic" should be deleted.

Signed and Sealed this
Seventh Day of February, 2012

David J. Kappos
*Director of the United States Patent and Trademark Office*